United States Patent
Argembeaux et al.

(10) Patent No.: US 9,820,930 B2
(45) Date of Patent: Nov. 21, 2017

(54) COSMETIC CLEANSING PREPARATIONS WITH NOVEL ASSOCIATIVE THICKENER

(71) Applicant: Beiersdorf AG, Hamburg (DE)

(72) Inventors: Horst Argembeaux, Wentorf (DE); Ursula Jensen, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 0 days.

(21) Appl. No.: 14/432,813

(22) PCT Filed: Sep. 10, 2013

(86) PCT No.: PCT/EP2013/068665
§ 371 (c)(1),
(2) Date: Apr. 1, 2015

(87) PCT Pub. No.: WO2014/053284
PCT Pub. Date: Apr. 10, 2014

(65) Prior Publication Data
US 2015/0283056 A1    Oct. 8, 2015

(30) Foreign Application Priority Data

Oct. 4, 2012 (DE) .......... 10 2012 218 091

(51) Int. Cl.
| | | |
|---|---|---|
| C11D 1/00 | (2006.01) | |
| C11D 3/37 | (2006.01) | |
| A61Q 19/10 | (2006.01) | |
| A61K 8/81 | (2006.01) | |
| A61Q 5/02 | (2006.01) | |
| A61K 8/02 | (2006.01) | |
| A61K 8/04 | (2006.01) | |

(52) U.S. Cl.
CPC .......... *A61K 8/8152* (2013.01); *A61K 8/0241* (2013.01); *A61K 8/042* (2013.01); *A61Q 5/02* (2013.01); *A61Q 19/10* (2013.01); *A61K 2800/262* (2013.01); *A61K 2800/28* (2013.01); *A61K 2800/654* (2013.01)

(58) Field of Classification Search
CPC .... A61K 8/0241; A61K 8/042; A61K 8/8152; A61K 2800/28; A61K 2800/262; C11D 1/00; C11D 3/37; C11D 3/3757; A61Q 19/10
See application file for complete search history.

(56) References Cited

U.S. PATENT DOCUMENTS

| | | |
|---|---|---|
| 6,242,531 B1 | 6/2001 | Craun |
| 6,635,702 B1 | 10/2003 | Schmucker-Castner et al. |
| 6,897,253 B2 | 5/2005 | Schmucker-Castner et al. |
| 7,153,496 B2 | 12/2006 | Tamareselvy et al. |
| 7,217,752 B2 | 5/2007 | Schmucker-Castner et al. |
| 7,288,616 B2 | 10/2007 | Tamareselvy et al. |
| 7,649,047 B2 | 1/2010 | Tamareselvy et al. |
| 2003/0202953 A1 | 10/2003 | Tamareselvy et al. |
| 2003/0207988 A1 | 11/2003 | Tamareselvy et al. |
| 2004/0087668 A1 | 5/2004 | Schmucker-Castner et al. |
| 2005/0158268 A1 | 7/2005 | Schmucker-Castner et al. |
| 2006/0251600 A1 | 11/2006 | Tamareselvy et al. |
| 2008/0045646 A1 | 2/2008 | Tamareselvy et al. |
| 2013/0203866 A1* | 8/2013 | Aleksandrovic-Bondzic ............... A61K 8/8152 514/772.6 |
| 2014/0336101 A1 | 11/2014 | Mertens |

FOREIGN PATENT DOCUMENTS

| | | | | |
|---|---|---|---|---|
| DE | 102010022063 | * | 12/2011 | ............... C08F 2/22 |
| DE | 102010022063 A1 | | 12/2011 | |
| DE | 102011078087 A1 | | 12/2012 | |
| EP | 1726331 A1 | | 11/2006 | |
| WO | 0176552 A2 | | 10/2001 | |
| WO | WO 01/76552 | * | 10/2001 | ............... A61K 7/50 |
| WO | 03061615 A1 | | 7/2003 | |
| WO | 03062288 A1 | | 7/2003 | |
| WO | 2004006870 A2 | | 1/2004 | |
| WO | 2007090759 A1 | | 8/2007 | |

OTHER PUBLICATIONS

Rheology Modifiers: "The Ingredients of Creativity Acusol TM Rheology Modifiers for Home and Fabric Care Products", May 1, 2008 (May 1, 2008) Retrieved from the Internet: URL:http://www.dow.comjassetsjattachments/ businessjacusol guidesjAcusolRheo low.pdf [retrieved on Feb. 18, 2014].

A et al: 11 Attorney General Madrid Files Lawsuit Against Six Auto Dealerships11 • US Fed News Service. Including US State News. Jan. 24, 2006 (Jan. 24, 2006). Retrieved from the Internet: URL:http:jjsearch.proquest.comjdocview/469724681 [retrieved on Feb. 18, 2014].

* cited by examiner

*Primary Examiner* — Brian P Mruk
(74) *Attorney, Agent, or Firm* — Abel Law Group, LLP

(57) ABSTRACT

The invention describes aqueous, surfactant-containing and/or transparent cleansing preparations containing novel associative thickeners, the A-MA polymers. Solid particles, bubbles and/or droplets can be present as a stable suspension in the preparations.

20 Claims, No Drawings

COSMETIC CLEANSING PREPARATIONS WITH NOVEL ASSOCIATIVE THICKENER

BACKGROUND OF THE INVENTION

1. Field of the Invention

The present invention describes transparent, surfactant-containing cleansing preparations which have a gel network and a pH<6.7. This gel network is formed with the help of novel associative thickeners, the A-MA polymers. This achieves a rheological profile that is very suitable for such cleansing preparations, as a result of which excellent product properties are achieved with regard to bottling, removal, foamability and spreadability. In particular, the stabilization of solid particles, droplets and bubbles is ensured in such preparations.

2. Discussion of Background Information

Although the prior art already recognizes preparations in which xanthan gum is used as a thickener, these preparations have cosmetic properties which can be improved as regards the skin feel during and after application. Moreover, only low viscosity values are achieved for an identical use concentration.

In order to make progress in the area of the stabilization of gel-like systems while simultaneously improving the application properties, experiments have been carried out in which xanthan gum has been replaced by polymeric structures. Crosslinked acrylate-based polymers have proven to be particularly suitable. When producing acrylate-based polymers, the selection of the monomers, the ratio of the monomers with one another and the course of the polymerization reaction play an important role. If associative monomers are present in an adequate amount in the selection of the monomers, then associative polymers are formed during the polymerization reactions.

Associative polymers are characterized by a hydrophobic end. The hydrophobic ends of the polymers can interact with one another and also with other hydrophobic components in a composition. In this way, hydrophobic regions are formed which can pass through a composition or be present in segments. A type of hydrophobic network is formed. In this way, the formation of the gel network is conceivable.

There are documents in the prior art in which the synthesis and/or the use of associative polymers are disclosed.

The U.S. Pat. No. 6,242,531 describes polymers which are polymerized from monomers with unsaturated ethylene groups. These monomers include monomers with carboxyl groups, long-chain alkyl esters of the acrylate or methacrylate and methyl or ethyl acrylate or methacrylate. The polymerization reaction takes place without organic solvents or diluents. The polymerization products can be used as thickeners, particularly in latex paints.

EP 1272159 discloses the use of acrylate crosspolymers which are composed of three structural components. These components comprise carboxylic acid monomers, such as for example acrylic acid, methacrylic acid or combinations of both substances, $\alpha,\beta$-ethylenically unsaturated monomers and polyunsaturated compounds. The acrylate crosspolymers thus obtained are available from B. F. Goodrich Company. These crosspolymers are used in stable, aqueous, surfactant-containing compositions, where an alkaline material is added to the compositions until a pH of 5 to 14 is reached and subsequently the addition of an acidic material takes place, during which the pH is lowered again to an acidic range.

EP 1465932 describes the synthesis of associative polymers of acidic vinyl monomers, nonionic vinyl monomers, a first associative monomer, a second associative monomer or semihydrophobic monomer and optionally a crosslinking monomer and/or a chain transfer agent. Furthermore, the use of these polymers inter alia in cosmetic preparations is described, with the addition of various cosmetic ingredients such as silicones, further polymers etc. being investigated.

WO 2003061615 discloses the applicability of various associative polymers in preparations for hair treatment. This specification describes the use of polymers of acidic vinyl monomers and associative monomers (HASE, hydrophobically modified alkali-swellable and alkali-soluble emulsion polymers) and polymers of acidic vinyl monomers, nonionic vinyl monomers, a first associative monomer, a second associative monomer or semihydrophobic monomer and optionally a crosslinking monomer and/or a chain transfer agent (ASAP, alkali-swellable and alkali-soluble associative polymers). These polymers make it possible for only one polymer to be used as thickener and simultaneously hair fixing agent.

WO 2007090759 discloses the production of multi-associative polymers which are obtained by emulsion polymerization of two different monomers. The monomers have the following common characteristics: an unsaturated region with a double bond, a polyoxyalkylene region and a hydrophobic region. The various monomers are characterized on the one hand by with an acid group and on the other hand by a hydrophobic group. Of the polymers thus obtained, one is suitable for use in cosmetic preparations.

All of these documents disclose the production of associative polymers and/or the use of these polymers in cosmetic preparations. Nevertheless, there is still a need for further associative polymers which have different or improved properties, such as the possibility of providing transparent liquid preparations which, if necessary, also allow the stable incorporation of particles, bubbles or drops. Moreover, the preparations should be easy to produce, easy to bottle and easy to remove from the packaging. Moreover, good foamability for cleansing preparations is an advantageous property which the consumer appreciates.

The document DE 102010022063 discloses the synthesis of an associative polymer by free-radical emulsion polymerization from an acidic vinyl monomer, a nonionic vinyl monomer, preferably a hydrophobic nonionic monomer, a monomer with unsaturated end group and polyoxyalkyl moiety, a crosslinking monomer and optionally a protective colloid.

Such polymers are obtainable in particular by free-radical emulsion polymerization of (A) at least one acidic vinyl monomer or salt thereof, (B) at least one nonionic vinyl monomer, particularly preferably a hydrophobic nonionic vinyl monomer, (C) at least one monomer containing an unsaturated end group and a polyoxyalkylene moiety, (D) at least one crosslinking monomer, (E) optionally a protective colloid, characterized in that the polymerization is controlled in such a way that at least at times the gel effect arises, achieved by the fact that the monomer addition (metering time) takes place over 40 minutes, particularly preferably over 30 minutes. In the event of such a polymerization utilizing the Trommsdorff effect, i.e. upon constant addition of the monomers and simultaneously high rate of addition of the monomers, a monomer excess is formed which leads to a self-acceleration of the polymerization (Trommsdorff effect). The result is an increase in the molecular weights coupled with advantageous morphology of the polymers. In this connection, it is particularly preferred if (F) associative monomers are missing or at most have a concentration of 15% by weight, preferably 10% by weight, particularly preferably 5% by weight, very particularly preferably 2.5% by weight, very extraordinarily preferably 1% by weight, very particularly extraordinarily preferably 0.1% by weight. It is particularly preferred if the acidic vinyl monomer (A) is selected from vinyl monomers with carboxyl groups, particularly preferably acrylic acid or methacrylic acid or alkali metal, alkaline earth metal, ammonium or alkylammonium salts thereof, very particularly preferably methacrylic acid or the alkali metal, alkaline earth metal, ammonium or alkylammonium salts thereof. It is particularly preferred if the nonionic vinyl monomer (B) is selected from C1-C22-alkyl (meth)acrylates and mixtures thereof. As a result, good flow properties and therefore an advantageous rheological profile are achieved. Additional long-chain alkyl acrylates (C12 and C18) are particularly preferred because they increase the achievable viscosity. It is particularly preferred if the monomer (C) comprising an unsaturated end group and a polyoxyalkylene moiety is selected from vinylpolyalkylene glycols or polymerizable surfactants or mixtures thereof, is particularly preferably selected from 8307 (Emulsogen® 8307 (Clariant), EO/PO 30 1,4-butandiol vinyl ether (EO/PO 30 mol)), RAL307 (Emulsogen® RAL307 (Clariant), allylpolyalkylene glycol ether (EO 30 mol)), A11/1800 (Polyglycol A11/1800 (Clariant), allylpolyalkylene glycol ether (EO 20 mol, PO 20 mol)), R1100 (Polyglycol R1100 (Clariant), vinylpolyalkylene glycol ether (EO 20 mol)), A111R (Pluriol® A111R (BASF), allyl alcohol alkoxylate), AB25-8 (Polyglycol AB/25-8 (Clariant), polyalkylene glycol allyl butyl ether (EO 25 mol, PO 8 mol)). It is particularly preferred if the crosslinking monomer (D) is selected from polyol (meth) acrylates with at least two (meth)acrylate groups and the mixed esters of polyols with acrylic acid and/or methacrylic acid. It is further particularly preferred if the monomers (A) are present in contents of from 10 to 75%, preferably 30 to 50%, particularly preferably 35 to 49%, (B) are present in contents of from 10 to 90%, preferably 30 to 80%, particularly preferably 47 to 60%, (C) are present in contents of from 0.5 to 40%, preferably 1 to 10%, particularly preferably 2 to 6%, (D) are present in contents of up to 1%, preferably 0.05 to 0.5%, particularly preferably 0.1 to 0.35%. It is very particularly preferred if the monomers (A):(B) are present in mass ratios of from 1:2 to 2:1.

It has been found that the morphology of the polymers produced by a rapid metered addition of the monomer mixture is advantageous in the context of the present invention. Polymers have different properties if the dosing time is varied. The dosing time is preferably 40 minutes and particularly preferably 30 minutes.

The polymers obtained in this way can be used for example in order to provide cosmetic cleansing products. The polymers thus obtained are referred to hereinbelow A-MA polymers.

The teaching for producing the A-MA polymers listed above and also the totality of the disclosure of DE 102010022063 are hereby incorporated into the disclosure of this application.

SUMMARY OF THE INVENTION

It has now surprisingly been found for the person skilled in the art that aqueous, surfactant-containing and/or transparent preparations comprising one or more A-MA polymer(s) overcome the disadvantages of the prior art.

In particular, cleansing preparations comprising at least one A-MA polymer are provided for human application.

According to the invention, preference is given to the use of at least one of the A-MA polymers 22, 24, 25, 28, 35, 37, 40 and/or 52, the production of which has likewise been disclosed in DE 102010022063.

According to the invention, it is likewise preferred if the concentration of at least one A-MA polymer is 0.5 to 15.0%, preferably 1.0 to 4.0%, particularly preferably 1.8 to 2.5% by weight, based on the active content of the polymer or polymers and the total weight of the preparation.

According to the invention, it is likewise preferred if further polymers are present besides one or more A-MA polymer(s). Furthermore, it is in accordance with the invention if the concentration of A-MA polymers and further polymers together is 0.5 to 15%, preferably 1.0 to 4.0%, particularly preferably 1.8 to 3.0%, based on the active content of the polymer or polymers and the total weight of the preparation. It is also in accordance with the invention that the further polymer or polymers are present with a content of from 0.01 to 14.5% by weight.

Likewise in accordance with the invention are cosmetic preparations comprising at least one A-MA polymer which comprise solid particles, droplets and/or bubbles which are, and also remain, suspended in largely stable form in the preparation. In particular, it is advantageous if the preparations according to the invention are cosmetic preparations, in particular cleansing preparations. Furthermore, it is preferred if the preparations according to the invention are aqueous, surfactant-containing and/or transparent preparations. Furthermore, it is in accordance with the invention if the content of at least one A-MA polymer is 0.5 to 15.0%, preferably 1.0 to 4.0%, particularly preferably 1.8 to 2.5% by weight, based on the active content of the polymer or polymers and the total weight of the preparation.

It is also in accordance with the invention if the solid particles are present in the form of particles and/or peeling bodies. The solid particles have in the preparations according to the invention a content of 0.005 to 15% by weight, preferably 0.1 to 10% by weight and particularly preferably 0.15 to 7.5% by weight, based on the total weight of the preparation. The particles, droplets or bubbles have a diameter of from 0.1 to 2000 μm, also a density of from 0.001 to 2000 g/cm$^3$.

It is likewise in accordance with the invention that the preparations described above have a pH<6.7, preferably 5.8 to 6.4.

According to the invention, it is also preferred that the preparations described above have a viscosity of from 1500 to 8000 mPa·s.

It is likewise in accordance with the invention that the preparations comprise at least 2.0% anionic surfactants, based on the total weight of the preparation.

Furthermore, it is in accordance with the invention that the anionic surfactants are used in combination with amphoteric and/or nonionic surfactants.

It is likewise in accordance with the invention that the preparations are transparent, the transparency being described by turbidity values which are below 20 NTU.

Also in accordance with the invention are shower gels, face cleansers, shampoos or cosmetic hydrogels comprising at least one A-MA polymer.

Also in accordance with the invention is the use of the preparations according to the invention for cosmetic application.

Also in accordance with the invention is the use of the above-described preparations for cleansing the skin, in particular the human skin.

The use of at least one A-MA polymer for producing aqueous, surfactant-containing cleansing preparations which form a gel network is in accordance with the invention.

Also in accordance with the invention is the use of at least one A-MA polymer for producing aqueous, surfactant-containing and/or transparent cleansing preparations.

Likewise in accordance with the invention is also the use of at least one A-MA polymer for producing aqueous, surfactant-containing and/or transparent cleansing preparations which have a pH<6.7.

Also in accordance with the invention is the use of at least one A-MA polymer for producing preparations which comprise solid particles, bubbles and/or droplets in largely stably suspended form. In particular, it is advantageous if the preparations according to the invention are cleansing preparations. Furthermore, it is advantageous if the preparations according to the invention are aqueous, surfactant-containing and/or transparent. It is very particularly advantageous if the preparations according to the invention are used in the field of cosmetics and here preferably as cleansing preparations.

Furthermore in accordance with the invention is the use of at least one A-MA polymer, where the content of at least one A-MA polymer is 0.5 to 15.0%, preferably 1.0 to 4.0%, particularly preferably 1.8 to 2.5%, based on the active content of the polymer or polymers and the total weight of the preparation.

Also in accordance with the invention is the use of at least one A-MA polymer for producing preparations which comprise solid particles, bubbles and/or droplets in stably suspended form, where the content of solid particles, bubbles and/or droplets is 0.005 to 15% by weight, preferably 0.1 to 10% by weight and particularly preferably 0.15 to 7.5% by weight, based on the total weight of the preparation.

The viscosity values which are disclosed in the present specification have been measured using the Rheomat R123 from the company ProRheo at 25° C. When measuring using the Rheomat R123, the rotor of the instrument is immersed bubble-free into the sample up to the mark.

The turbidity values that are disclosed in the present specification have been measured using a turbidity measuring device, with distilled water with a value of NTU=0 serving as standard.

Further Polymers:

For the purposes of thickening the preparations according to the invention and for stabilizing particles, further polymers can optionally be used which can be selected from the group of the polysaccharides or derivatives thereof, e.g. hyaluronic acid, and hydroxypropylmethylcellulose and particularly advantageously from the group of the polyacrylates, preferably a polyacrylate from the group of the so-called Carbopols, for example Carbopol grades 980, 981, 1382, 2984, 5984, RT, Ultrez 2020, Ultrez 10, in each case individually or in combination.

Surfactants:

The surfactants which are used in the preparations according to the invention can be anionic surfactants in combination with amphoteric, nonionic and/or cationic surfactants.

Anionic surfactants to be used advantageously are
Acylamino acids (and salts thereof), such as
1. Acylglutamates, for example sodium acylglutamate, sodium cocoylglutamate, di-TEA palmitoylaspartate and sodium caprylic/capric glutamate,
2. Acyl peptides, for example palmitoyl-hydrolyzed milk protein, sodium cocoyl-hydrolyzed soya protein and sodium/potassium cocoyl-hydrolyzed collagen,
3. Sarcosinates, for example myristoyl sarcosine, TEA lauroyl sarcosinate, sodium lauroylsarcosinate and sodium cocoylsarcosinate,
4. Taurates, for example sodium lauroyltaurate and sodium methylcocoyltaurate,
5. Acyllactylates, lauroyllactylate, caproyllactylate,
6. Alaninates.

Carboxylic acids and derivatives, such as
1. Carboxylic acids, for example lauric acid/salt, aluminum stearate, magnesium alkanolate and zinc undecylenate, stearic acid/salt, palmitic acid/salt,
2. Esters of the carboxylic acids, for example calcium stearoyllactylate, laureth-6 citrate and sodium PEG-4 lauramide carboxylate,
3. Ethers of the carboxylic acids, for example sodium laureth-13 carboxylate and sodium PEG-6 cocamide carboxylate, Phosphoric acid esters and salts, such as for example DEA oleth-10 phosphate and dilaureth phosphate, Sulfonic acids and salts, such as
1. Acyl isethionates, e.g. sodium/ammonium cocoylisethionate, sodium lauroyl methylisethionate,
2. Alkylarylsulfonates,
3. Alkylsulfonates, for example sodium cocomonoglyceride sulfate, sodium C12-14 olefinsulfonate, sodium lauryl sulfoacetate and magnesium PEG-3 cocamide sulfate,
4. Sulfosuccinates, for example dioctylsodiumsulfosuccinate, disodium laureth sulfosuccinate, disodium lauryl sulfosuccinate, disodium undecylenamido-MEA sulfosuccinate and PEG-5 lauryl citrate sulfosuccinate, and Sulfuric acid esters, such as
1. Alkyl ether sulfates with different degrees of ethoxylation and mixtures thereof, for example sodium, ammonium, magnesium, MIPA, TIPA laureth-X sulfate, sodium myreth-X sulfate and sodium C12-13-pareth-X sulfate, where X=1-5 ethoxy groups
2. Alkyl sulfates, for example sodium, ammonium and TEA lauryl sulfate, sodium, ammonium and TEA-cocosulfate.

Amphoteric surfactants to be used advantageously are
1. Acyl/dialkylethylenediamine, for example sodium acylamphoacetate, disodium acylamphodipropionate, disodium alkylamphodiacetate, disodium cocoamphodiacetate, disodium cocoamphomonoacetate, sodium acylamphohydroxypropylsulfonate, disodium acylamphodiacetate and sodium acylamphopropionate,
2. N-alkylamino acids, for example aminopropylalkylglutamide, alkylaminopropionic acid, sodium alkylimidodipropionate and lauroamphocarboxyglycinate.
3. Betaines, for example coco betaine, cocoamidopropylbetaine
4. Sultaines, for example laurylhydroxysultaine Nonionic surfactants to be used advantageously are
1. Alcohols,
2. Alkanolamides, such as cocamide MEA/DEA/MIPA,
3. Amine oxides, such as cocoamidopropylamine oxide,
4. Esters which are formed by esterification of carboxylic acids with ethylene oxide, glycerol, sorbitan or other alcohols,
5. Ethers, for example ethoxylated/propoxylated alcohols, laureth-X where X=2-10 ethoxy groups, ethoxylated/propoxylated esters, ethoxylated/propoxylated glycerol esters, PEG-200 hydrogenated glyceryl palmate, PEG- 120 methyl glucose dioleate, ethoxylated/propoxylated cholesterols, ethoxylated/propoxylated triglyceride esters, ethoxylated propoxylated lanolin, ethoxylated/propoxylated polysiloxanes, propoxylated POE ethers and alkyl polyglycosides such as lauryl glucoside, decyl glycoside and cocoglycoside.

6. Sucrose esters, sucrose ethers
7. Polyglycerol esters, diglycerol esters, monoglycerol esters
8. Methylglucose esters, esters of hydroxy acids.

Advantageous anionic surfactants are, for example, sodium laureth sulfate and sodium myreth sulfate. Sodium laureth sulfate is available for example from BASF under the trade name Texapon® N 70. Sodium myreth sulfate is available for example from BASF under the trade name Texapon® K 14 S Spezial.

Advantageous amphoteric surfactants are for example betaines, particularly preferably cocoamidopropyl betaine, which is available for example as Tego® Betain F 50 from Evonik.

Advantageous nonionic surfactants are for example alkyl glucosides, particularly preferably lauryl glucosides. These surfactants are available for example from BASF under the trade name Plantacare® 1200 UP.

UV Filters:

It is advantageous in the context of the present inventions to add sunscreen filters to the preparations. However, the primary purpose of these preparations is not protection against sunlight, but they nevertheless comprise a content of UV protection substances.

It is advantageous in the context of the present invention if the UV filter substances used are water-soluble.

Water-soluble UV filter substances according to the invention are e.g.:

Salts of 2-phenylbenzimidazole-5-sulfonic acid, such as its sodium, potassium or its triethanolammonium salt, and also the sulfonic acid itself;

Sulfonic acid derivatives of 3-benzylidenecamphor, such as e.g. 4-(2-oxo-3-bornylidenemethyl)benzenesulfonic acid, 2-methyl-5-(2-oxo-3-bornylidene-methyl)sulfonic acid and salts thereof.

Furthermore, oil-soluble UV filters bonded to polymers, such as e.g. polysilicone-15, which is also available under the trade name Parsol SLX, can.

In the context of the present invention, it is preferred for example to use benzophenone-4.

The total amount of the filter substances is from the range from 0.01 to 30% by weight, preferably 0.02 to 10% by weight—in each case based on the total weight of the preparations.

Solvents:

The preparations according to the invention can optionally advantageously comprise alcohols, diols or polyols of low carbon number, and ethers thereof, preferably ethanol, isopropanol, 1,2-propanediol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

Preservatives:

To preserve the present preparations, the preservatives customarily used in cosmetics can be used. These include on the one hand compounds which are approved as preservatives in food technology, such as, for example, parabens. On the other hand, preservatives and preservative auxiliaries customary in cosmetics can also be used, such as dibromodicyanobutane (2-bromo-2-bromomethylglutaronitrile), 3-iodo-2-propynyl butylcarbamate, 2-bromo-2-nitropropane-1,3-diol, imidazolidinylurea, 5-chloro-2-methyl-4-isothiazolin-3-one, 2-chloroacetamide, benzalkonium chloride, benzyl alcohol and phenylhydroxyalkyl ethers, for example phenoxyethanol.

pH Adjustment:

The pH can be adjusted in the manner customary in the cosmetics industry. However, preference is given to using citric acid and sodium hydroxide in order to establish the required pH.

Particles:

Particles in the context of the present specification are particles from all organic and inorganic solids on a natural or synthetic basis. Use is made e.g. of plastic particles for example made of viscose, cellulose, polypropylene, polyester, polyethylene terephthalate (PET), polytetrafluoroethylene (PTFE), aramid, nylon, kevlar, polyvinyl derivatives, polyurethanes, polystyrene, cellulose esters and/or polyethylene, and all other types of ground stone, ground plant constituents such as nut shells and kernels.

Mixtures of different particles are also contemplated, which are pelleted by suitable physical processes such as e.g. compression. Preference is given for example to Unispheres® from Induchem or Cosmospheres® from Pelletech.

It is naturally known to the person skilled in the art that cosmetic preparations are in most cases inconceivable without the customary auxiliaries and additives. The cosmetic preparations according to the invention can accordingly also comprise cosmetic auxiliaries, as are customarily used in such preparations, for example perfumes, substances for preventing foaming, dyes, pigments which have a coloring effect, emulsifiers, softening, antiinflammatory substances, insect repellants, bactericides, viricides, salts, antimicrobially, proteolytically or keratolytically effective substances or other customary constituents of a cosmetic formulation such as foam stabilizers and electrolytes.

The preparations according to the invention, illustrated in exemplary terms by the following examples, are characterized by the fact that the preparations are easy to bottle into suitable packagings and can be removed easily from the respective packaging. When using the preparations according to the invention for example as shower preparation, the foamability is rapid and a creamy foam is formed. The spreadability of the preparations according to the invention on the skin and/or the hair is easy and quick. If solid particles, bubbles and/or droplets have been incorporated into the preparations according to the invention, these particles, bubbles and/or droplets are in largely stably suspended form and also remain in largely stably suspended form.

DETAILED DESCRIPTION OF THE INVENTION

Examples:
Transparent Shower Gel with Particles:

| Component | 1 | 2 | 3 | 4 |
|---|---|---|---|---|
| Polymer[1] | 7.0 | 6.9 | 7.5 | 6.5 |
| Texapon N70[2] | 9.30 | 11.20 | 9.10 | 12.9 |
| Tego Betain F 50[3] | 13.20 | 14.30 | 13.00 | 8.8 |
| Sodium hydroxide, 45% strength | q.s. to establish pH = 5.9-6.3 | q.s. to establish pH = 6.0-6.4 | q.s. to establish pH = 5.8-6.2 | q.s. to establish pH = 6.1-6.5 |

-continued

| Component | 1 | 2 | 3 | 4 |
|---|---|---|---|---|
| Cremophor RH 40[4] | 0.80 | 0.80 | 0.80 | 0.80 |
| Perfume | q.s. | q.s. | q.s. | q.s. |
| Preservative | q.s. | q.s. | q.s. | q.s. |
| Water | ad 100.00 | ad 100.00 | ad 100.00 | ad 100.00 |
| Tegosoft GC[5] | 1.75 | 1.75 | 1.75 | 1.0 |
| Hostapon CCG[6] | 2.00 | 2.40 | 1.75 | — |
| Rewoderm Li 520-70[9] | — | — | — | 0.5 |
| Trisodium EDTA | 1.00 | 1.00 | 1.00 | 1.00 |
| Benzophenone-4 | 0.05 | 0.05 | 0.05 | 0.05 |
| Helianthus Annuus Seed Oil | 0.10 | 0.10 | 0.10 | 0.10 |
| Particle[12] | 0.15 | 0.15 | 0.15 | 0.15 |

The quantitative data are data in percent by weight, based on the total weight of the preparation.

Transparent Facial Cleanser with Particles:

| Component | 1 | 2 | 3 |
|---|---|---|---|
| Polymer[1] | 7.50 | 7.25 | 7.80 |
| Texapon K14S Spezial[7] | 4.20 | 4.50 | 4.20 |
| Plantacare 1200 UP[8] | 1.90 | 2.00 | 1.85 |
| Tego Betain F 50[3] | 11.80 | 12.10 | 11.65 |
| Rewoderm LI 520-70[9] | 0.70 | 0.70 | 0.70 |
| Cremophor RH 40[4] | 0.50 | 0.50 | 0.50 |
| Sodium hydroxide | q.s. to establish pH = 6.0-6.4 | q.s. to establish pH = 6.0-6.4 | q.s. to establish pH = 6.0-6.4 |
| Perfume | q.s. | q.s. | q.s. |
| Preservative | q.s. | q.s. | q.s. |
| Water | ad 100.00 | ad 100.00 | ad 100.00 |
| Trisodium EDTA | 0.50 | 0.50 | 0.50 |
| Ucare Polymer JR 400[10] | 0.10 | 0.10 | 0.10 |
| Panthenol | 0.10 | 0.10 | 0.10 |
| Benzophenone-4 | 0.05 | 0.05 | 0.05 |
| Particle | 0.30 | 0.30 | 0.30 |

The quantitative data are data in percent by weight, based on the total weight of the preparation.

Transparent Cleanser with Peeling Bodies:

| Component | 1 | 2 | 3 |
|---|---|---|---|
| Polymer[1] | 7.50 | 7.30 | 7.60 |
| Texapon K14S Spezial[7] | 4.20 | 4.35 | 4.15 |
| Plantacare 2000[11] | 2.00 | 2.20 | 1.95 |
| Tego Betain F 50[3] | 11.80 | 12.40 | 11.75 |
| Rewoderm Li 520-70[9] | 3.00 | 3.00 | 3.00 |
| Cremophor RH 40[4] | 0.50 | 0.50 | 0.50 |
| Sodium hydroxide | q.s. to establish pH = 6.0-6.4 | q.s. to establish pH = 6.0-6.4 | q.s. to establish pH = 6.0-6.4 |
| Perfume | q.s. | q.s. | q.s. |
| Preservative | q.s. | q.s. | q.s. |
| Water | ad 100.00 | ad 100.00 | ad 100.00 |
| Trisodium EDTA | 0.50 | 0.50 | 0.50 |
| Ucare Polymer JR 400[10] | 0.10 | 0.10 | 0.10 |
| Magnesium chloride | 0.10 | 0.10 | 0.10 |
| Benzophenone-4 | 0.05 | 0.05 | 0.05 |
| Alcohol, denatured | 1.00 | 1.00 | 1.00 |
| Menthol | 0.10 | 0.10 | 0.10 |
| Tocopheryl acetate | 0.10 | 0.10 | 0.10 |
| Particle[12] and peeling agents[13] | 6.15 | 6.15 | 6.15 |

The quantitative data are data in percent by weight, based on the total weight of the preparation.

[1] = A-MA polymer; 30%
[2] = Sodium laureth sulfate, 70%, BASF
[3] = Cocamidopropyl betaine, 34%, Evonik
[4] = PEG-40 hydrogenated castor oil, BASF
[5] = PEG-7 glyceryl cocoate, Evonik
[6] = Disodium cocoyl glutamate, 25%, Clariant
[7] = Sodium myreth sulfate, 70%, BASF
[8] = Lauryl polyglucose, 51.5%, BASF
[9] = PEG-200 hydrogenated glyceryl palmate, Evonik
[10] = Polyquaternium-10, Dow Chemical
[11] = Decylglucoside, 53%, BASF
[12] = Active-ingredient-containing particles, e.g. Unispheres from Permcos
[13] = Abrasive bodies, e.g. polyethylene powder from Inducem

What is claimed is:

1. An aqueous, surfactant-containing, cosmetic preparation, wherein the preparation is transparent and comprises one or more associative A-MA polymers and one or more additional polymers which comprise at least one polymer selected from polysaccharides and derivatives thereof, hyaluronic acid, hydroxypropylmethylcellulose, polyquaternium-10, and polyacrylates.

2. The preparation of claim 1, wherein the preparation comprises an active content of from 1.0% to 4.0% by weight of the one or more A-MA polymers.

3. The preparation of claim 1, wherein the preparation comprises an active content of from 1.8% to 2.5% by weight of the one or more A-MA polymers.

4. The preparation of claim 1, wherein the one or more additional polymers comprise at least one polymer selected from polysaccharides and derivatives thereof.

5. The preparation of claim 4, wherein the one or more additional polymers comprise at least one polymer selected from hyaluronic acid, hydroxypropylmethylcellulose and polyquaternium-10.

6. The preparation of claim 1, wherein the one or more additional polymers comprise one or more polyacrylates.

7. The preparation of claim 2, wherein the preparation comprises from 0.01% to 14.5% by weight of the one or more additional polymers.

8. The preparation of claim 1, wherein the preparation further comprises one or more of solid particles, gas bubbles, liquid droplets stably suspended therein.

9. The preparation of claim 8, wherein solid particles are present in the form of peeling agents or peeling bodies.

10. The preparation of claim 9, wherein the preparation comprises from 0.15% to 7.5% by weight of solid particles.

11. An aqueous, cosmetic preparation, wherein the preparation is transparent and comprises one or more associative A-MA polymers and one or more surfactants comprising one or more alkyl glucosides.

12. The preparation of claim 11, wherein the preparation comprises lauryl glucoside.

13. The preparation of claim 11, wherein the preparation comprises an active content of from 1.8% to 2.5% by weight of the one or more A-MA polymers.

14. The preparation of claim 11, wherein the preparation further comprises one or more of solid particles, gas bubbles, liquid droplets stably suspended therein.

15. The preparation of claim 14, wherein solid particles are present in the form of peeling agents or peeling bodies.

16. The preparation of claim 15, wherein the preparation comprises from 0.15% to 7.5% by weight of solid particles.

17. An aqueous, surfactant-containing, cosmetic preparation, wherein the preparation is transparent and comprises one or more associative A-MA polymers and one or more UV filter substances.

18. The preparation of claim 17, wherein the one or more UV filter substances comprise benzophenone-4.

19. The preparation of claim 17, wherein the one or more UV filter substances are present in a concentration of from 0.02% to 10% by weight, based on a total weight of the preparation.

20. The preparation of claim 17, wherein the preparation further comprises one or more of solid particles, gas bubbles, liquid droplets stably suspended therein.

\* \* \* \* \*